April 19, 1960 N. J. NUTE Plant Pat. 1,936
BLACKBERRY PLANT
Filed May 9, 1958
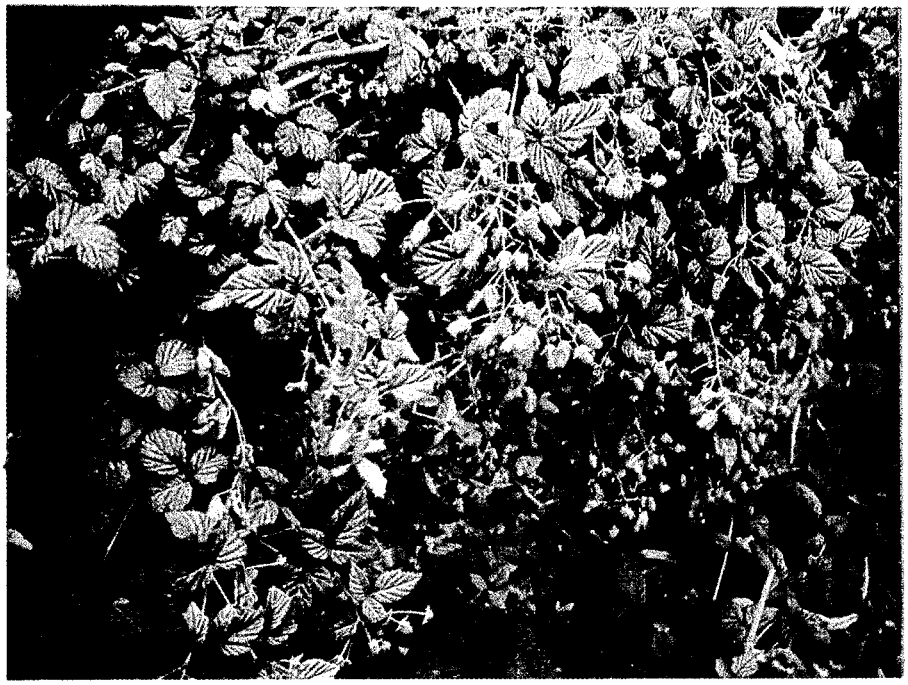
Norwood J. Nute
INVENTOR.
BY Clarence A. O'Brien and Harvey B. Jacobson
Attorneys United States Patent Office Plant Pat. 1,936
Patented Apr. 19, 1960

1,936

BLACKBERRY PLANT

Norwood J. Nute, Siletz, Oreg.

Application May 9, 1958, Serial No. 734,375

1 Claim. (Cl. 47—62)

The present invention relates to an improved blackberry and plant.

This plant was discovered by me as a seedling. As a result of definite breeding efforts carried on by me since 1951 at Siletz, Oregon, it was originated by open pollination with the native trailing blackberry.

Subject variety parent was found growing as a seedling on my farm in the town of Siletz, county of Lincoln, State of Oregon. This plant was moved and reset in my boysenberry field within a few feet of a thornless loganberry plant. Three years later and after the field had been left unattended for two years, I discovered this new berry growing beside and beneath the parent plant, which had come up from seeds of old dried berries. This subject variety plant was then taken and placed by itself, and the ends of new canes were covered with soil (layered). These cane tip ends later produced young plants which were used for the trial tests. This was repeated for three years, each time taking plants from the last generation, and each year planting the new plant farther from the parent plant. Thus, after three series of clonal propagations, subject variety produced this outstanding berry. Reproduction is also made by cutting canes in pieces, leaving a leaf bud (scion) on each piece of cane. These are covered with moist soil and during the summer and fall months these pieces of cane reproduce plants. Propagation by these methods is one of the distinguishing characteristics of this new variety. Such asexual reproduction occurred at my farm in the town of Siletz, county of Lincoln, State of Oregon.

Prolonged tests and observation of my new variety show that the berry is very rich and mild-flavored, containing less acid than most other blackberries. Further, as compared to either Logan (unpatented) or boysenberry, my berry will tolerate more freezing weather, will stand more sultry weather without sun scald, and will hold up longer on the vine when fully ripe. It has fruiting laterals at each leaf bud, often as many as four; fruit spurs (clusters) put well to the sunlight, fruiting from the ground up to end of canes.

The canes put out many large laterals, often 25 feet long. The berry has a heavy core that breaks down completely in freezing, making it outstanding as frozen fruit. The berry is very sweet when fully ripe and is also very firm, thus making it an excellent shipper. The berry will stand two or three days of hard rain when fully ripe without any damage, and will hold up to twelve days on the vine when fully ripe.

Subject variety responds readily to sprays in this manner: When the disease "leaf spot" makes appearance in the tender spring foliage, a spray mixture of copper and hydrated lime protects new leaves from infection without injury to the foliage; also subject variety will not be injured by a solution of 4 to 8 gallons of lime and sulphur to 100 gallons of water applied on the dormant canes from March 1st to March 15th.

*Immune to "root weevil"*

Subject variety was planted in a strawberry field on sodland that was completely destroyed by root weevil. This strawberry field was plowed, but not treated in any way to kill the root weevil, and subject variety was planted directly in these weevils. Subject grew strong and without any noticeable damage. Upon examination of the root system in the fall, there was no damage whatsoever from the root weevil. Subject variety showed no root weevil damage on this planting one and two years later. Subject thus appears to be immune to root weevil, a most destroying insect or grub.

*Resistance to disease*

Subject variety has much stronger resistance to yellow rust (orange rust), cane rot (this is a common disease on the west coast of the United States which attacks the canes while on the ground in the winter or during the wet months when the canes are lying in rotting weeds or grasses. This disease leaves a portion of the underside of the cane black; the sap rots and often the disease will encircle the entire cane in a small area), and root rot, than Cascade (unpatented) or boysenberry. For three years, on our farm, yellow rust damaged the boysenberries very badly, and the Cascade had some damage from this disease. Even the grass in the subject variety field was damaged badly, but subject variety had only a very light trace on first leaves at the crown. No cane rot has been found even on land where subject variety has been completely covered with water for a period of three weeks, and water has stood within three inches of top of soil for three months during winter. Boysenberry was killed out under this condition, and Cascade suffered very heavy cane rot.

*Subject variety in comparison to the Cascade variety*

Subject variety has smaller seed cells, tighter and firmer than Cascade and withstands more summer heat and wet weather when fully ripe than Cascade; fruit is sweeter and the size of fruit will average ¼ to ½ inch larger in length and ¼ inch larger in diameter at cap than Cascade; subject variety canes are much more pliable and nearly thornless in comparison to Cascade.

In summary, the primary characteristics of my new variety are as follows:

(1) Ripens all the berries out to sunlight.
(2) Holds up well on the vine in excess of ten days when fully ripe.
(3) Stands more sun heat without scalding than other berries.
(4) Stands more rain when fully ripe than most other cane berries.
(5) Loosens well at the cap for easy harvest without finger bruising.
(6) Extra heavy production. Has fruit laterals at every node, often as many as four, with each cluster bearing from 13 to 27 large, uniform berries.
(7) Very small, soft seeds.
(8) Firm, meaty fruit.
(9) Mild flavor of Zielinski (unpatented) and Logan combined.
(10) Very little acid.

The following is a detailed description of the new variety:

Parentage: Seedling.
*Seed parent.*—Native wild Oregon blackberry.
*Pollen parent.*—Unknown, possibly loganberry or boysenberry.
Classification: Botanic—native trailing blackberry.

Propagation: Holds its distinguishing characteristics through propagation by layer and scion.

Plant: Growth—new growth starts late in spring to give grower sufficient time for training after all spring freezing has past. Will stand better than 5° below zero without any freeze damage. Bush is very strong, and very hardy. The canes are nearly thornless, smooth and stocky. Laterals are smooth and have small spines. Color of laterals is purplish, covered with purplish bloom, and are attached at a 45° angle upward. The number of lenticeles (air cells) are undetectable by sight. The bush has no suckers. The canes are ¾″ at the base up to 25 feet long and very hardy. Spreads. Bushes are in full production by their second year.

Foliage: Has heavy foliage, with leaves 4″ to 7″ long and 7″ to 10″ wide. The upper surface of the leaf is forest green-deep olive, with the under surface being light green. It is triangular in shape and has velvety texture with serrated edges. Peticles are 1″ to 1½″ in length, deep olive in color and very strong growth.

Flowers: Blooms from May 10 to June 15 with hardy bloom. Flowers are white in color, ¾″ to 1″ in diameter. Has 6 to 8 petals, nearly double with center of light yellow. Not pubescent.

Buds: The buds are ⅛″ in diameter, ⅛″ long, very hardy and pubescent. Calyx is brownish-green color, ¼″ to ⅜″ long.

Petals: Petals are oval shape, ¼″ long, white in color.

*Anthers.*—Short, oval shape, with whitish yellow color.

*Filaments.*—Short, round shape, very light green in color.

*Pistils.*—Oblong shape, very light green color.

Canes: Very strong, are ¾″ at base and are up to 25 feet long. Canes, after two years, appear to be smooth and very nearly thornless. Tough and pliable and will not break while training on trellis. Very strong resistance to disease, immune to root weevil and responds readily to sprays. New growth starts late in spring to give grower ample time for training after all spring freezing has past.

Berry: Outside—the berry is from ½″ to ¾″ in diameter and from 1¼″ to 2″ in length. Has very mild blackberry with loganberry flavor, with aroma of native blackberry. It is very deep wine in color. Its shape is long with blunt end, and ripens from the 10th of July until the 26th of August. The berry loosens at the cap when ripe, with round, blunt apex. The skin is thin. It bears regularly with average harvest period of from four to six weeks. Inside—flesh of berry is deep wine color, of excellent quality, very juicy with tight, very firm texture. Produces up to 30 lbs. per hill, averaging 18 lbs. This berry is very firm, making it an excellent shipping berry.

Seeds: Very small, ⅛″ to 1/32″, kidney shaped and number 85 per berry, are brown in color.

Thorns: Main canes nearly thornless, few soft, mossy like thorns after second year.

I claim:

A new and distinct variety of blackberry plant substantially as herein shown and described, characterized particularly by its exceptional productivity and resistance to heat and cold, the delectable flavor of its fruit, and the retention of its fruit in prime condition after ripening for a period in excess of ten days.

No references cited.